United States Patent
Missling et al.

(10) Patent No.: US 11,771,707 B2
(45) Date of Patent: *Oct. 3, 2023

(54) PHARMACEUTICAL COMPOSITIONS AND USES THEREOF

(71) Applicant: SpineThera, Plymouth, MN (US)

(72) Inventors: Jeffrey Missling, Eden Prairie, MN (US); Emily R. Rolfes Meyering, Saint Louis Park, MN (US); Henry Meyer, Minneapolis, MN (US); Celeste Ondich, Brooklyn Center, MN (US)

(73) Assignee: SPINETHERA, Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/247,820

(22) Filed: Dec. 23, 2020

(65) Prior Publication Data

US 2021/0186988 A1   Jun. 24, 2021

Related U.S. Application Data

(63) Continuation of application No. 16/343,642, filed as application No. PCT/US2016/059544 on Oct. 28, 2016, now Pat. No. 10,925,883.

(51) Int. Cl.
  *A61K 31/573* (2006.01)
  *A61K 9/00* (2006.01)
  *A61K 9/16* (2006.01)
  *A61K 9/19* (2006.01)

(52) U.S. Cl.
  CPC .......... *A61K 31/573* (2013.01); *A61K 9/0019* (2013.01); *A61K 9/1647* (2013.01); *A61K 9/19* (2013.01)

(58) Field of Classification Search
  CPC .. A61K 31/573; A61K 9/0019; A61K 9/1647; A61K 9/19
  See application file for complete search history.

(56) References Cited

U.S. PATENT DOCUMENTS

| 8,927,529 | B2 | 1/2015 | Missling et al. |
| 10,925,883 | B2 | 2/2021 | Missling et al. |
| 2003/0099682 | A1 | 5/2003 | Moussy et al. |
| 2008/0031958 | A1 | 2/2008 | Sakurai et al. |
| 2011/0206773 | A1* | 8/2011 | Lavik .................. A61K 31/573 514/180 |
| 2013/0195933 | A1 | 8/2013 | Missling |
| 2014/0343155 | A1 | 11/2014 | Jayaraman et al. |
| 2019/0269698 | A1 | 9/2019 | Missling et al. |

FOREIGN PATENT DOCUMENTS

| AU | 2016428204 B2 | 1/2020 |
| CA | 3042009 | 5/2020 |
| CN | 101188989 A | 5/2008 |
| CN | 110099677 A | 8/2019 |
| CN | 114146057 A | 3/2022 |
| EP | 3515404 B1 | 3/2020 |
| IN | 201917020767 A | 8/2019 |
| JP | H06293636 A | 10/1994 |
| JP | H09221418 A | 8/1997 |
| JP | 2010155849 A | 7/2010 |
| JP | 2013513616 A | 4/2013 |
| JP | 2019533716 A | 11/2019 |
| JP | 6712003 B2 | 6/2020 |
| KR | 20090116494 A | 11/2009 |
| KR | 102135537 B1 | 7/2020 |
| WO | WO-2011072218 A2 | 6/2011 |
| WO | WO-2011080733 A1 | 7/2011 |
| WO | WO-201 2071480 A2 | 5/2012 |
| WO | WO-201 2110886 A1 | 8/2012 |
| WO | WO-201 4170186 A1 | 10/2014 |
| WO | WO-201 5113782 A1 | 8/2015 |
| WO | WO-2018080521 A1 | 5/2018 |

OTHER PUBLICATIONS

U.S. Appl. No. 16/343,642, U.S. Pat. No. 10,925,883, filed Apr. 19, 2019, Pharmaceutical Compositions and Uses Thereof.
"U.S. Appl. No. 16/343,642, Final Office Action dated Jun. 26, 2020", 12 pgs.
"U.S. Appl. No. 16/343,642, Non Final Office Action dated Mar. 13, 2020", 11 pgs.
"U.S. Appl. No. 16/343,642, Non Final Office Action dated Jul. 30, 2020", 11 pgs.
"U.S. Appl. No. 16/343,642, Notice of Allowability dated Jan. 27, 2021", 2 pgs.
"U.S. Appl. No. 16/343,642, Notice of Allowability dated Oct. 15, 2020", 2 pgs.
"U.S. Appl. No. 16/343,642, Notice of Allowability dated Nov. 24, 2020", 2 pgs.
"U.S. Appl. No. 16/343,642, Notice of Allowance dated Sep. 21, 2020", 7 pgs.
"U.S. Appl. No. 16/343,642, Preliminary Amendment filed Apr. 19, 2019", 7 pgs.
"U.S. Appl. No. 16/343,642, Response filed Feb. 7, 2020 to Restriction Requirement dated Dec. 30, 2019", 6 pgs.
"U.S. Appl. No. 16/343,642, Response filed Jun. 3, 20 to Non Final Office Action dated Mar. 13, 2020", 10 pgs.
"U.S. Appl. No. 16/343,642, Response filed Jul. 9, 2020 to Final Office Action dated Jun. 26, 2020", 6 pgs.

(Continued)

*Primary Examiner* — Snigdha Maewall
(74) *Attorney, Agent, or Firm* — SCHWEGMAN LUNDBERG & WOESSNER, P.A.

(57) ABSTRACT

Embodiments of the present invention are directed to a plurality of substantially spherical microspheres comprising at least one API substantially dispersed in at least one polymer and a lyoprotectant on an outside surface of the plurality of substantially spherical microspheres, wherein the plurality of substantially spherical microspheres have a D99[num] particle diameter of less than about 10 µm; a D90[num] circularity value of from about 0.8 to about 1.0; and comprise API in a weight of about 20 to about 40 wt. % of the polymer. Other embodiments relate to injectable compositions comprising such microspheres and methods of treating a number of conditions by administering such injectable compositions to a subject.

21 Claims, 2 Drawing Sheets

(56) References Cited

OTHER PUBLICATIONS

"U.S. Appl. No. 16/343,642, Response filed Aug. 12, 2020 to Non Final Office Action dated Jul. 30, 2020", 6 pgs.
"U.S. Appl. No. 16/343,642, Restriction Requirement dated Dec. 30, 2019", 8 pgs.
"U.S. Appl. No. 16/343,642, Supplemental Preliminary Amendment filed Sep. 19, 2019", 5 pgs.
"Australian Application Serial No. 2016428204, First Examination Report dated May 31, 2019", 2 pgs.
"Australian Application Serial No. 2016428204, Response filed Sep. 4, 2019 to First Examination Report dated May 31, 2019", 1 pg.
"Australian Application Serial No. 2016428204, Voluntary Amendment and PPH Request filed May 27, 2019", 6 pgs.
"Brazil Application Serial No. BR1120190084932, Office Action datedd Oct. 20, 2020", w/out English translation, 4 pgs.
"Canadian Application Serial No. 3,042,009, Office Action dated Jul. 8, 2019", 3 pgs.
"Canadian Application Serial No. 3,042,009, Response filed Aug. 8, 2019 to Office Action dated Jul. 8, 2019", 8 pgs.
"Canadian Application Serial No. 3,042,009, Voluntary Amendment and PPH Request filed Apr. 26, 2019", 13 pgs.
"Chinese Application Serial No. 201680091189.7, Office Action dated Jan. 3, 2020", W/English Translation, 13 pgs.
"Chinese Application Serial No. 201680091189.7, Office Action dated Sep. 10, 2020", w/English Translation, 18 pgs.
"Chinese Application Serial No. 201680091189.7, Response filed Jul. 20, 2020 to Office Action mailed Jan. 3, 2020", w/ current English claims, claims not amended in response, 9 pgs.
"Chinese Application Serial No. 201680091189.7, Voluntary Amendment and PPH Request filed Aug. 19, 2019", W/ English claims, 6 pgs.
"Indian Application Serial No. 201917020767, First Examination Report dated Feb. 26, 2020", 6 pgs.
"Indian Application Serial No. 201917020767, Response filed Aug. 26, 20 to First Examination Report dated Feb. 26, 2020", 68 pgs.
"Indian Application Serial No. 201917020767, Voluntary Amendment filed Jul. 5, 2019", in English, 9 pgs.
"Indonesian Application Serial No. PID201904228, Office Action dated Sep. 8, 2020", w/o English translation, 3 pgs.
"International Application Serial No. PCT/US2016/059544, International Preliminary Report on Patentability dated Jan. 21, 2019", 18 pgs.
"International Application Serial No. PCT/US2016/059544, International Search Report dated Jan. 25, 2017", 3 pgs.
"International Application Serial No. PCT/US2016/059544, Written Opinion dated Jan. 25, 2017", 5 pgs.
"International Application Serial No. PCT/US2016/059544, Written Opinion of the International Preliminary Examining Authority dated Oct. 2, 2018", 5 pgs.
"International Application Serial No. PCT/US2016/059544, Response Filed Nov. 30, 2018 to Written Opinion of the International Preliminary Examining Authority dated Oct. 2, 2018", 7 pgs.
"Israel Application Serial No. 266205, Office Action dated Sep. 16, 2019", w/ English translation, 6 pgs.
"Israel Application Serial No. 266205, Response filed Jan. 12, 2020 to Office Action dated Sep. 16, 2019", w/ current English claims, claims not amended in response filed, 5 pgs.

"Japanese Application Serial No. 2019-529880, Notification of Reasons for Refusal dated Oct. 8, 2019", w/ English translation, 6 pgs.
"Japanese Application Serial No. 2019-529880, Response filed Feb. 14, 2020 to Notification of Reasons for Refusal dated Oct. 8, 2019", w/ current English claims, claims not amended in response filed, 7 pgs.
"Japanese Application Serial No. 2019-529880, Voluntary Amendment and PPH Request filed May 31, 2019", w/ English claims, 9 pgs.
"Korean Application Serial No. 10-2019-7015121, Notice of Preliminary Rejection dated Nov. 6, 2019", W/English Translation, 10 pgs.
"Korean Application Serial No. 10-2019-7015121, Response filed Jan. 31, 2020 to Notice of Preliminary Rejection dated Nov. 6, 2019", w/ English claims, 19 pgs.
"Korean Application Serial No. 10-2019-7015121, Voluntary Amendment and PPH Request filed May 27, 2019", w/ English claims, 6 pgs.
"Mexican Application Serial No. MX/a/2019/004830, Office Action dated Mar. 17, 2020", w/o English Translation, 4 pgs.
"Mexican Application Serial No. MX/a/2019/004830, Response filed Sep. 14, 2020 to Office Action dated Mar. 17, 2020", w/ English claims, 4 pgs.
"Mexican Application Serial No. MX/a/2019/004830, Voluntary Amendment filed Mar. 6, 2020", w/ English claims, PPH Request and Voluntary Amendment filed, 49 pgs.
"Philippines Application Serial No. 1-2019-500947, Voluntary Amendment and PPH Request filed May 7, 2019", w/ English claims, 5 pgs.
"South African Application Serial No. 2019/03341, Amendment filed May 29, 2020", 7 pgs.
"Chinese Application Serial No. 201680091189.7, Office Action dated Mar. 26, 2021", w English translation, 13 pgs.
"Chinese Application Serial No. 201680091189.7, Response filed Jul. 31, 2021 to Office Action dated Mar. 26, 2021", w English claims, 11 pgs.
"Chinese Application Serial No. 201680091189.7, Decision of Rejection dated Aug. 18, 2021", w English translation, 8 pgs.
"Chinese Application Serial No. 201680091189.7, Response filed Jan. 19, 2021 to Office Action dated Sep. 10, 2020", w English claims, 14 pgs.
"Brazil Application Serial No. BR1120190084932, Response filed Feb. 1, 2021 to Office Action dated Oct. 20, 2020", w English claims, 18 pgs.
"Chinese Application Serial No. 202111429195.8, Office Action dated Jul. 4, 2022", W English Translation, 12 pgs.
"Filipino Application Serial No. 1-2019-500947, Substantive Examination Report dated Jun. 23, 2022", 4 pgs.
"Filipino Application Serial No. 1-2019-500947, Response filed Aug. 19, 2022 to Substantive Examination Report dated Jun. 23, 2022", W English Claims, 9 pgs.
"Chinese Application Serial No. 202111429195.8, Voluntary Amendment filed Jun. 2, 2022", W/English Claims, 8 pgs.
"Chinese Application Serial No. 201680091189.7, Notice of Reexamination dated Jul. 25, 2023", W English Translation, 13 pgs.
"Chinese Application No. 202111429195.8, Response Filed Jun. 5, 2023 to Decision of Rejection dated Feb. 23, 2023", W English Claims, 16 pgs.

* cited by examiner

PHARMACEUTICAL COMPOSITIONS AND USES THEREOF

PRIORITY APPLICATIONS

This application is a continuation of U.S. patent application Ser. No. 16/343,642, filed on Apr. 19, 2019, which is a U.S. National Stage Filing under 35 U.S.C. 371 from International Application No. PCT/US2016/059544, filed on Oct. 28, 2016, and published as WO2018/080521 on May 3, 2018; the benefit of priority of each of which are hereby claimed, and which applications and publications are hereby incorporated herein by reference in their entirety.

BACKGROUND

Patients who suffer from certain conditions (e.g., lower back pain and related discomforts, including sciatica) are sometimes treated with compositions that are injected into a space in the body (e.g., muscle or the epidural space). It is not uncommon for patients to receive two or three injections over the period of several months, which increases the risk of medical complications and can also be costly, inconvenient, and time-consuming.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1:
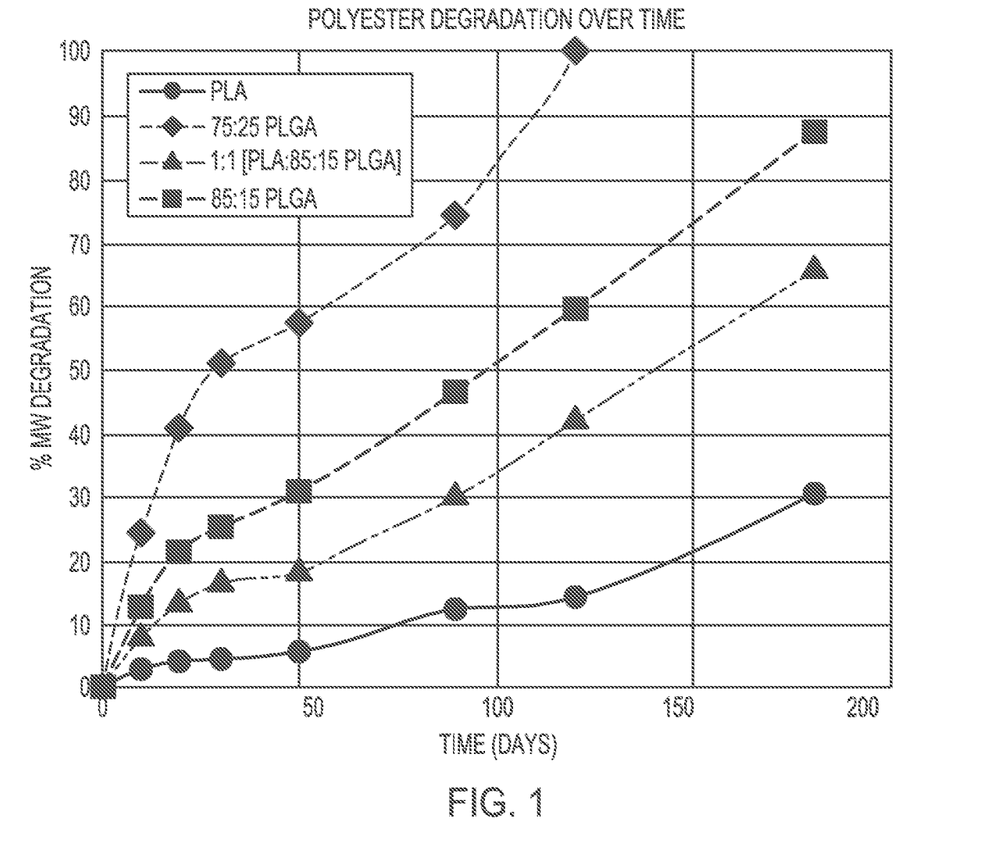
FIG. 1 is a plot of degradation rates of microspheres made of poly(lactic acid) (PLA), poly(lactic-co-glycolic acid) (PLGA 75:25), a blend of PLA and PLGA (85:15), and PLGA (85:15).
Figure 2:
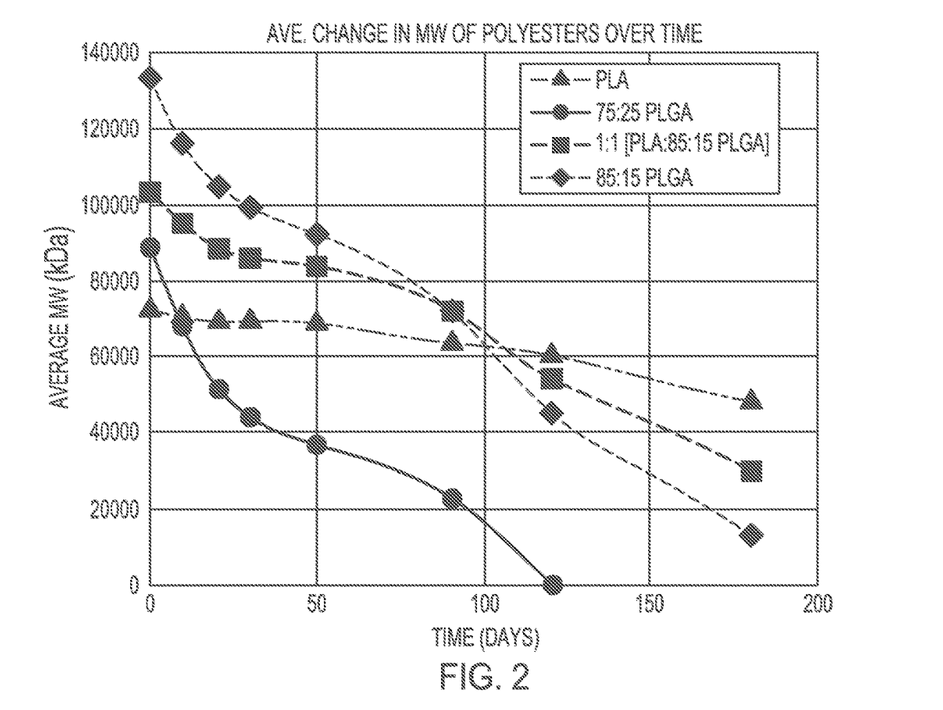
FIG. 2 is a plot of the average change in $M_w$ as a function of time microspheres made of PLA, PLGA (75:25), a blend of PLA and PLGA (85:15), and PLGA (85:15).
Figure 3:
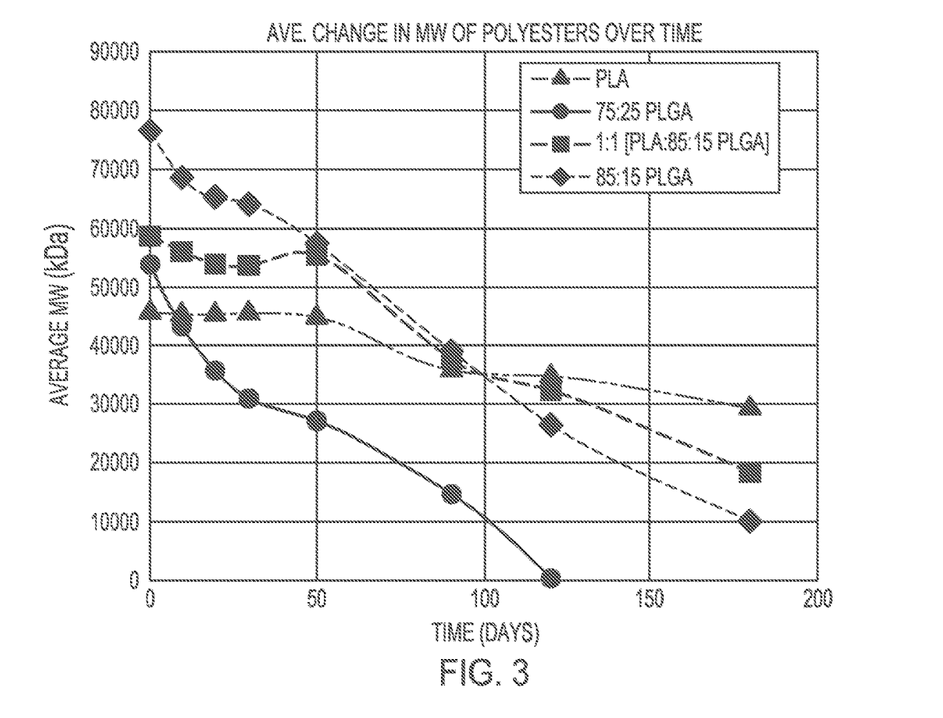
FIG. 3 is a plot of the average change in $M_w$ as a function of time microspheres made of PLA, PLGA (75:25), a blend of PLA and PLGA (85:15), and PLGA (85:15).

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

The present disclosure generally relates to injectable compositions comprising microspheres comprising at least one active pharmaceutical ingredient (API) dispersed therein. In some embodiments, the injectable compositions further comprise, among other things (e.g., excipients), a vehicle.

The microspheres described herein have several advantageous features. These microsphere features can include one or more of the following:
- exhibit a sustained period of release of the API;
- exhibit a substantially controlled, low burst release of the API(s) described herein:
- do not substantially aggregate when suspended in the injection vehicle, even after a prolonged period of time;
- are non-thrombogenic;
- can be provided separately from the vehicle and reconstituted at, e.g., the point of care;
- can easily be combined with the vehicle by hand (e.g., shaking), vortex or other equipment (e.g., single- or dual-barrel syringe) to ensure substantially complete mixing with the vehicle;
- can have a high drug load;
- are stable and are long-lasting post-injection, such that one injection allows for fewer repeat injections to treat a subject (e.g., a human subjects or animal subjects, such as primates, dogs, cats, pigs, cows, horses, sheep, and the like);
- are small enough to move through capillaries;
- allow for local pain relief, when the API(s) in the microspheres are intended to treat pain; and
- are generally easy to use.

In some embodiments, the injectable compositions described herein are flowable. As long as the microspheres do not occlude arteries or veins when injected, it is within the purview of suitable, flowable injectable compositions. In some embodiments, the vehicle is a liquid vehicle. In other embodiments, the vehicle is a flowable, bioresorbable polymer such as polylactic acid, polyglycolic acid, polylactic-co-glycolic acid, polylactic acid-co-caprolactone, polyethylene glycol, polyethylene oxide, poly lactic acid-block-poly ethylene glycol, poly glycolic acid-block-poly ethylene glycol, poly lactide-co-glycolide-block-poly ethylene glycol, poly ethylene glycol-block-lipid, polyvinyl pyrrolidone, poly vinyl alcohol, a glycosaminoglycan, polyorthoesters, polysaccharides, polysaccharide derivatives, polyhyaluronic acid, polyalginic acid, chitin, chitosan, chitosan derivatives, cellulose, hydroxyethylcellulose, hydroxypropylcellulose, carboxymethylcellulose, polypeptides, polylysine, polyglutamic acid, albumin, polyanhydrides, polyhydroxy alkonoates, polyhydroxy valerate, polyhydroxy butyrate, proteins, polyphosphate esters, lipids, and mixtures thereof.

The injectable compositions described herein, as well as the microspheres comprised therein, are substantially non-pyrogenic.

In some embodiments, the injectable compositions described herein include: microspheres comprising an API substantially dispersed in a polymer, wherein the surface of the microspheres is hydrophilic; and a hydrophilic vehicle; wherein the microspheres are substantially dispersible in the vehicle. In alternative embodiments, the injectable compositions described herein include: microspheres comprising an API substantially dispersed in a polymer, wherein the surface of the microspheres is hydrophobic; and a hydrophobic vehicle; wherein the microspheres are substantially dispersible in the vehicle.

As used herein, the term "substantially dispersed in a polymer" and "substantially dispersed in the polymer" generally means that the API is mixed in with the polymer inside of the microsphere. The API may be mixed evenly throughout the inside of the microsphere or may be present in pockets of drug within the microsphere. These phrases also mean that there are no discernible solid forms (e.g., crystals) of the API on any portion of the surface of each microsphere. In some embodiments, at least one API is substantially dispersed in the polymer and the composition is otherwise substantially free of API that is insoluble in the injection vehicle. Scanning electron microscopy (SEM) is at least one method that can be used to evaluate the presence or lack of presence of free drug or other solids on the surface of a microsphere.

The vehicle present in the injectable compositions described herein can be any vehicle suitable for the delivery of the injectable compositions to a desired site or sites. Vehicles include, but are not limited to, saline, sterile water, Ringer's solutions, and isotonic sodium chloride solutions. Examples of vehicles include, but are not limited to, Sodium Chloride Injection USP (0.9%), Ringer's Injection USP, Lactated Ringer's Injection USP, Sodium Lactate Injection USP, Dextrose Injection USP (5% or 10%), Bacteriostatic Water for Injection USP and Sterile Water for Injection USP.

In some embodiments, the vehicle can be a hydrophilic, liquid vehicle comprising substances that are suitable and appropriate for use as a liquid vehicle. In some embodiments, the hydrophilic, liquid vehicle can include water.

In other embodiments, the vehicle can be a hydrophobic, liquid vehicle comprising substances that are suitable and appropriate for use as a liquid vehicle. For example, the hydrophobic, liquid vehicle can include at least one of an oil derived from a living species (e.g., plant-derived oils, such as vegetable oils including, but are not limited to almond oil, babassu oil, black currant seed oil, borage oil, canola oil, castor oil, coconut oil, corn oil, cottonseed oil, olive oil, peanut oil, palm oil, palm kernel oil, rapeseed oil, safflower oil, soybean oil, sunflower oil and sesame oil; or animal, such as squalene), an oil derived from a silicone-containing oil, and a synthetic hydrophobic liquid. Other hydrophobic vehicles include castor oil, squalane, diethylene glycol monoethyl ether, propylene glycol, isostearyl isostearate, isopropyl myristate, dipropylene glycol dimethyl ether, diethylene glycol, dipropylene glycol, mineral oil, silicone oil, caprylic/capric triglycerides, cetyl alcohols, and stearyl alcohols.

The injectable compositions contemplated herein can, but need not, comprise pharmaceutically acceptable excipients including antioxidants, buffering agents, salts, lyoprotectants, anti-blocking agents, chelating agents, dispersing agents, electrolytes, emulsifiers, neutralizing agents, preservatives, stabilizing agents, surface tension reducers, surfactants, anti-foaming agents, tonicity agents, viscosity modulating agents, and combinations thereof. In some embodiments, one or more of these components can act in a variety of ways, including as aids in reducing agglomeration when the microspheres described herein are lyophilized; and/or stabilize suspensions of microspheres in the injectable compositions, such that the microspheres do not settle or agglomerate in any substantial way in storage or in use. In some embodiments, one or more of these components can act in a variety of ways, including making packaging and/or reconstitution more facile.

Anti-foaming agents include silicones, such as polydimethyl siloxane, glycol polysiloxane, methylphenol polysiloxane, trialkyl or tetraalkyl silanes, hydrophobic silica defoamers and mixtures thereof; and cyclodextrins.

Buffering agents include HEPES and those prepared from a suitable combination of the acid and/or base forms of acetates, citrates, phosphates, carbonates, succinates, and borates, such as sodium citrate dihydrate and boric acid. Phosphate buffers may be composed of sodium phosphate dibasic and sodium phosphate monobasic. Examples include monosodium phosphate, monohydrate, sodium phosphate dibasic heptahydrate, and sodium phosphate monobasic monohydrate. Buffering agents may be provided in any of the compositions in an amount effective to control the pH of the composition. The injectable compositions can have any suitable and appropriate pH. In specific embodiments, the injectable compositions can have a pH of less than about 8.5. In additional specific embodiments, the injectable compositions can have a pH of about 7.0 to about 8.5; about 3.0 to about 6.5; about 3.5 to about 5.0; about 6 to about 8.5; about 7 to about 8; about 7 to about 7.6; or about 7.5 to about 8. The inclusion of a buffer can depend on the chemistry or environmental factors (pH, etc.) of the intended target physiology.

Lyoprotectants include excipients added to significantly prevent or reduce chemical and/or physical instability of the microspheres upon lyophilization and subsequent storage and/or to reduce the aggregation of the microspheres during the drying process and during process steps in which the microspheres are handled in the dry form. Useful lyoprotectants include, but are not limited to, sugars and their corresponding sugar alcohols; an amino acid such as monosodium glutamate or histidine; salts such as sodium chloride and sodium bicarbonate; a methylamine such as betaine; a lyotropic salt such as magnesium sulfate; a polyol such as trihydric or higher molecular weight sugar alcohols, e.g. glycerin, dextran, erythritol, glycerol, arabitol, xylitol, sorbitol, and mannitol; propylene glycol; polyethylene glycol; Pluronics®; and combinations thereof. Additional examples of lyoprotectants include, but are not limited to, glycerin and gelatin, and the sugars mellibiose, melezitose, raffinose, mannotriose and stachyose. Examples of reducing sugars include, but are not limited to, glucose, maltose, lactose, matulose, iso-matulose and lactulose. Examples of non-reducing sugars include, but are not limited to, non-reducing glycosides of polyhydroxy compounds selected from sugar alcohols and other straight chain polyalcohols. Examples of sugar alcohols include, but are not limited to, monoglycosides, compounds obtained by reduction of disaccharides such as lactose, maltose, lactulose and maltulose. The glycosidic side group can be either glucosidic or galactosidic. Additional examples of sugar alcohols include, but are not limited to, glucitol, maltitol, lactitol and iso-maltulose.

In some embodiments, the least one API substantially dispersed in at least one polymer and the lyoprotectant is on an outside surface of the plurality of substantially spherical microspheres. As used herein, "on an outside surface" generally refers to (i) lyoprotecant that is on an outside surface, in direct contact with an outside surface of the plurality of substantially spherical microspheres; and/or (ii) free lyoprotectant present along with the plurality of substantially spherical microspheres, but is not in direct contact with an outside surface of the plurality of substantially spherical microspheres.

Chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. In some instances, the chelating agent(s) can act as substances that reduce the surface tension of the injectable compositions described herein.

Dispersing agents and/or viscosity modulating agents are materials that can control the diffusion and homogeneity of the injectable compositions. The injectable compositions described herein can comprise one or more dispersing agents, including dispersed within the microspheres described herein. But, in some embodiments, the dispersing agents can be removed from the injectable compositions, from the microspheres or both, via methods known in the art. Examples of dispersing agents include, but are not limited to, hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA; commercially known as Mowiol®), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronic F127, Pluronics F68®, F88®, and F108®, which are block copolymers of ethylene oxide and propylene oxide); and poloxamines (e.g., Tetronic 908, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, alginates, chitosans or combinations thereof. Plasticizers such as cellulose or triethyl cellulose are also be used as dispersing agents. Other dispersing agents include dimyristoyl phosphatidyl choline, phosphatidyl cholines (c8-c18), phosphatidylethanolamines (c8-c18), phosphatidyl glycerols (c8-c18), natural phosphatidyl choline from eggs or soy, natural phosphatidyl glycerol from eggs or soy, cholesterol and isopropyl myristate.

Preservatives include benzalkonium chloride, PURITE®, sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, methyl and ethyl parabens, methylparaben, polyvinyl alcohol, benzyl alcohol, phenylethanol, hexetidine, and chlorite components.

Salts include those having sodium, potassium or ammonium cations and chloride, citrate, ascorbate, borate, phosphate, bicarbonate, sulfate, thiosulfate or bisulfite anions. Suitable salts include sodium chloride, potassium chloride, sodium thiosulfate, sodium bisulfite and ammonium sulfate.

Tonicity agents include glycerin, sugar alcohols, xylitol, sorbitol, glycerol, erythritol, mannitol, monosaccharides, disaccharides, trisaccharides, oligosaccharides, polysaccharides, salts, potassium chloride and/or sodium chloride. Tonicity agents may be provided in an amount effective to control the tonicity or osmolality of the compositions. The osmolality of the composition can be in a range of about 200 to about 400, or about 250 to about 350, mOsmol/kg respectively. In one embodiment, the composition is isotonic. An isotonic solution is a solution that has the same solute concentration as that inside normal cells of the body and the blood. An isotonic solution in contact with a cell produces no net flow of water across the cell membrane.

Surfactants include cationic, anionic, zwitterionic, and nonionic surfactants. Cationic surfactants include, for example, cetytrimethylammonium bromide or "CTAB" (e.g., cetrimide), benzalkonium chloride, DDA (dimethyl dioctodecyl ammonium bromide), and DOTAP (dioleoyl-3-trimethylammonium-propane), among others. Anionic surfactants include, for example, SDS (sodium dodecyl sulfate). SLS (sodium lauryl sulfate), DSS (disulfosuccinate), and sulphated fatty alcohols, among others. Nonionic surfactants include, for example, PVA (polyvinyl alcohol), povidone (also known as polyvinylpyrrolidone or PVP), sorbitan esters, polysorbates, polyoxyethylated glycol monoethers, polyoxyethylated alkyl phenols, and poloxamers, among others.

Defoaming agents include excipients added to reduce foam formation in the microsphere-injection vehicle suspension. Defoaming agents may be hydrophobic or hydrophilic and are largely insoluble in the injection vehicle. Useful defoaming agents include natural oils, synthetic oils, glycols, poly-glycols, and combinations thereof. Specific examples of defoaming agents include polydimethylsiloxane, cottonseed oil, propylene glycol, dipropylene glycol, and polyethylene glycol.

The injectable compositions described herein can be formulated to provide a desired or requisite rate of release of the API(s). In some embodiments, the injectable compositions can be formulated to provide a sustained release of the incorporated API(s). In additional embodiments, the injectable compositions can be formulated to provide a more immediate release of API. In additional specific embodiments, the injectable compositions can be formulated to provide an extended release of API(s). In additional specific embodiments, the injectable compositions can be formulated to provide a modified release of API(s). In additional specific embodiments, the injectable compositions can be formulated to provide a combination (or mixture or hybrid) release of API. In some embodiments, if the injectable compositions described herein comprise two or more APIs, each API can be tailored to release at similar or varying rates of release depending on the conditions to be treated. Thus, for example, if the injectable compositions comprise two APIs, one API could be released at a faster rate than the other.

The injectable compositions described herein can be formulated to provide a controlled 'burst' release of API on the range of less than 30% (e.g., less than about 25%, less than about 20%; less than about 15%; less than about 10%; less than about 5%; less than about 2% or less than about 1%; about 1% to about 30%; about 2% to about 30%; about 2% to about 15%; about 1% to about 5%; about 1% to about 10%; or about 2% to about 5%) following administration (e.g., about two hours following administration) of the injectable compositions to a subject (e.g., a human or animal subject). In some embodiments, injectable compositions described herein can be formulated to provide a controlled "burst" release of API on the range of from about 2% to about 5% in about two hours following administration of the injectable compositions to a subject. In other embodiments, the diffusion of drug out of the microspheres may be delayed for a period of time prior to "burst" release occurring. Delayed diffusion of drug may be between 30 minutes and 18 hours; about 1 to about 12 hours; about 2 to about 8 hours; or about 3 to about 6 hours.

In an alternative or complementary embodiment, the injectable compositions described herein can be formulated to provide long-lasting release of the API over a period of from about 14 to about 120 days (e.g., from about 45 to about 60 days; from about 30 to about 90 days; or from about 45 to about 75 days), independent of the site of delivery of the injectable compositions.

In still other embodiments, the injectable compositions described herein can be formulated to provide release of about 2% to about 30% (e.g., about 10% to about 30%; about 15% to about 30%; about 2% to about 15%; about 2% to about 10%; about 20% to about 30%; or about 10% to about 25%) of at least one API, from a plurality of microspheres in a vehicle, within 48 hours (e.g., within 6 hours, within 12 hours, within 18 hours, within 24 hours, within 30 hours, within 36 hours, or within 42 hours) following administration of an injectable composition to a subject; and release the at least one API over a period of from about 14 to about 120 days (e.g., from about 45 to about 60 days; from about 30 to about 90 days; or from about 45 to about 75 days).

Sites for delivery of the injectable compositions of the various embodiments described herein include the epidural space (e.g., to treat back pain); fluid-filled cavities (e.g., ocular and ophthalmic sites, including sub-retinal sites); conjunctival sites; sites where accidental intravenous and intraarterial injections might occur; transnasal sites for delivery of drugs across the blood-brain-barrier; intrathecal sites; intramuscular sites, including near nerves to which one might wish to deliver an anti-inflammatory; intra-discal; sites along the central spinal canal; facet joint sites; intraarticular spaces, including the ankle, elbow, hip, knee, shoulder, spine, and wrist; transdermal sites; oral sites; subcutaneous sites; intranasal sites; vaginal sites; buccal sites; dental sites; intratumoral sites; intramuscular sites; intravenous sites; or sites in the head/skull. These sites can be located on a human or animal subject.

Other sites for the delivery of the injectable compositions of the various embodiments described herein include nerves or sites near nerves including the greater occipital nerve(s), the lesser occipital nerve(s), the third occipital nerve(s), greater auricular nerve(s), transverse cervical nerve(s), the supraclavicular nerve(s), and/or branches of any of these nerves. Targeting such nerves can be useful in the treatment of headache, generally, and in the treatment of migraine headaches, cluster headaches, tension-type headaches, chronic daily headache, facial pain, and other medical, psychiatric, and neurological conditions and disorders including: pain resulting from one or more medical conditions including, but not limited to: migraine headaches, migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder; musculoskeletal neck pain: reflex sympathetic dystrophy, cervicalgia; glossodynia, carotidynia; cricoidynia; otalgia due to middle ear lesion: gastric pain; sciatica; maxillary neuralgia; laryngeal pain, myalgia of neck muscles; trigeminal neuralgia; post-lumbar puncture headache; low cerebrospinal fluid pressure headache: temporomandibular joint disorder; atypical facial pain; ciliary neuralgia; paratrigeminal neuralgia; petrosal neuralgia: Eagle's syndrome: idiopathic intracranial hypertension; orofacial pain; myofascial pain syndrome involving the head, neck, and shoulder; chronic migraneous neuralgia, cervical headache; paratrigeminal paralysis; sphenopalatine ganglion neuralgia; carotidynia; Vidian neuralgia; and causalgia; epilepsy, including, but not limited to, generalized and partial seizure disorders; cerebrovascular diseases resulting from one or more medical conditions including, but not limited to, atherosclerosis, aneurysms, strokes, and cerebral hemorrhage; autoimmune diseases resulting from one or more medical conditions including, but not limited to, multiple sclerosis: sleep disorders resulting from one or more medical conditions including, but not limited to, sleep apnea and parasomnias; autonomic disorders resulting from one or more medical conditions including, but not limited to: gastrointestinal disorders, including, but not limited to, gastrointestinal motility disorders, nausea, vomiting, diarrhea, chronic hiccups, gastroesophageal reflux disease, and hypersecretion of gastric acid; autonomic insufficiency; excessive epiphoresis; excessive rhinorrhea; and cardiovascular disorders including, but not limited to, cardiac dysrhythmias and arrhythmias, hypertension, and carotid sinus disease; urinary bladder disorders resulting from one or more medical conditions including, but not limited to, spastic and flaccid bladder; abnormal metabolic states resulting from one or more medical conditions including, but not limited to, hyperthyroidism and hypothyroidism; disorders of the muscular system resulting from one or more medical conditions including, but not limited to, muscular dystrophy and spasms of the upper respiratory tract and face; neuropsychiatric disorders resulting from one or more medical conditions including, but not limited to, depression, schizophrenia, bipolar disorder, autism, personality disorders, and obsessive-compulsive disorder; urinary and fecal incontinence; and erectile or other sexual dysfunctions.

Other sites for the delivery of the injectable compositions of the various embodiments described herein include nerves or sites near nerves including the transgeminal sensory nerves, including the transgeminal nerve ophthalmic division, maxillary division, mandibular division, frontal branch, supra orbital nerve, supra trochlear nerve, infraorbital nerve, lacrimal nerve, nasociliary nerve, superior alveolar nerve, buccal nerve, lingual nerve, inferior alveolar nerve, mental nerve, auriculotemporal nerve, common peroneal nerve, common plantar digital nerves, femoral nerve, lateral plantar nerve, medial plantar nerve, peroneal communicating branch of musculocutaneous nerve, plantar digital nerves, posterior femoral cutaneous nerve, saphenous nerve, sciatic nerve, sural nerve, and tibial nerve.

The injectable compositions can have any suitable and appropriate volume. In various embodiments, it may be desirable to employ an injectable compositions having a relatively low volume, for patient safety, compliance, and comfort purposes. To that end, some embodiments are directed to injectable compositions that can have a total volume of less than about 50 mL (e.g., less than 20 mL; less than 15 mL; less than 10 mL; less than 5 mL; less than about 1 mL; about 1 to about 20 mL; about 1 to about 10 mL; about 1 to about 5 mL or about 2 to about 5 mL). In additional specific embodiments, the injectable compositions can have a total volume of less than about 5 mL. In some embodiments, the injectable compositions can have up to 500 mg of microspheres (e.g., from about 1 mg to about 100 mg microspheres; from about 5 mg to about 400 mg microspheres; from about 50 mg to about 500 mg microspheres; about 100 mg to about 500 mg microspheres; or about 50 mg to about 250 mg microspheres) per milliliter of vehicle.

In some embodiments, the dry, packaged microspheres can have a shelf-life of 1 year or more; 2 years or more; 3 years or more; 4 years or more; 5 years or more; about 1 year to about 5 years; about 1 year to about 2 years; or about 1 year to about 3 years, regardless of how the microspheres are stored (e.g., at temperatures of about 0° C. or below; at temperatures of from about 0° C. to about 5° C.; or at temperatures of from about 20° C. to about 40° C.).

The injectable compositions of the various embodiments described herein comprise microspheres comprising at least one active pharmaceutical ingredient (API) and a polymer. In some embodiments, the API is substantially dispersed in a polymer. In some embodiments, the microspheres are solid microspheres and do not have a hollow core. In other embodiments, the microspheres are core-shell structures, wherein the API forms the core of the microspheres and the polymer forms a shell substantially covering the API.

The polymer comprised in the microspheres of the various embodiments described herein can be any suitable biodegradable polymer. Non-limiting examples of polymers include poly(caprolactone) (PCL), ethylene vinyl acetate polymer (EVA), poly(lactic acid) (PLA), poly(L-lactic acid) (PLLA), poly(glycolic acid) (PGA), poly(lactic-co-glycolic acid) (PLGA), PLGA-poly(ethylene glycol) block copolymer; poly(L-lactic-I-glycolic acid) (PLLGA), poly(D,L-lactide) (PDLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyhydroxylalkanoates, poly(hydroxybutyrate) (P4HB), poly-L-lysine (PLL), poly-L-glutamic acid, poly (hydroxy acids), polyanhydrides, polyorthoesters, poly(ester amides), polyamides, poly(ester ethers), polycarbonates, polyphosphates, polyphosphoesters, polyphosphazines, polydioxazones, polyurethanes, derivatized celluloses such as alkyl celluloses, hydroxyalkyl celluloses, cellulose ethers, cellulose esters, nitro celluloses, hydroxypropylcellulose, carboxymethylcellulose, polyvinylalcohols, polyaminoacds, poly(butyric acid), poly(valeric acid), poly(levulinic acid), and combinations of one or more of the aforementioned polymers or block-copolymers of two or more of the aforementioned polymers.

In some embodiments (e.g., for >30 day extended-release formulations), the polymer is PLGA. In some embodiments, the lactic acid:glycolic acid ratio in a PLGA polymer is from about 50:50 to about 99:1 (e.g., from about 75:25 to about 90:10; about 70:30 to about 90:10; about or from about 80:20 to about 90:10; about 85:15 to about 75:25; about 85:15; or about 75:25). In some embodiments, the PLGA can have a weight average molecular weight ($M_w$) of from about 20 kDa to about 1000 kDa (e.g., from about 50 kDa to about 500 kDa; about 100 kDa to about 300 kDa; or about 150 kDa to about 250 kDa. In some embodiments, the PLGA can have a polydispersity index no greater than 3, no greater than 2.5, no greater than 2, or even no greater than about 1.8. In some embodiments the polymer has a glass transition temperature from about 25° C. to about 65° C., from about 30° C. to about 55° C., or from about 35° C. to about 50° C.

In some embodiments the polymer is PLA. In some embodiments, the PLA can have a weight average molecular weight ($M_w$) of from about 20 kDa to about 1000 kDa (e.g., from about 40 kDa to about 500 kDa; about 60 kDa to about 300 kDa; or about 80 kDa to about 250 kDa. In some embodiments, the PLA can have a polydispersity index no greater than 3, no greater than 2.5, no greater than 2, or even no greater than about 1.8.

In some embodiments, multi-block copolymers are also contemplated herein, including triblock copolymers of the biodegradable polymers listed herein.

In some embodiments the polymer is PLA/PLGA block copolymer. In some embodiments, the PLA/PLGA block copolymer can have a weight average molecular weight ($M_w$) of from about 10 kDa to about 300 kDa; about 20 kDa to about 200 kDa; or about 40 kDa to about 100 kDa. In some embodiments, the PLA/PLGA block copolymer can have a polydispersity index no greater than 3, no greater than 2.5, no greater than 2, or even no greater than about 1.8.

In some embodiments, blends of two or more polymers described herein are also contemplated. For example, blends of PLA and PLGA are contemplated, where the PLA is blended with the PLGA or the PLGA is blended with the PLA in about a range of ratios including 15:85, 25:75, 50:50, etc. For example, blends of PCL and PLGA are contemplated, where the PCL is blended with the PLGA or the PLGA is blended with the PLA in about a range of ratios including 15:85, 25:75, 50:50, etc.

In some embodiments, an extended release formulation includes one or more biodegradable polymers from the list hereinto allow for specific tuning of release and degradation characteristics. The biodegradable polymers can be in any form including uncapped polymers, wherein the termini are carboxylic acid termini; or capped polymers wherein the termini are partially or even fully capped as esters (e.g., as ($C_1$-$C_6$)alkyl esters, such as methyl, ethyl, propyl and butyl esters; ($C_6$-$C_{14}$)aryl-($C_1$-$C_6$)alkyl esters, such as benzyl and napthylmethyl esters; and combinations thereof). In some embodiments, the ($C_1$-$C_6$)alkyl and/or the ($C_6$-$C_{14}$)aryl portions of the cap can be substituted with one or more groups such as —$NR^1R^2$ groups, where $R^1$ and $R^2$ are independently selected from H, ($C_1$-$C_6$)alkyl, ($C_6$-$C_{14}$)aryl, and ($C_6$-$C_{14}$)aryl-($C_1$-$C_6$)alkyl groups). In other embodiments, the ($C_1$-$C_6$)alkyl and/or the ($C_6$-$C_{14}$)aryl portions of the cap can be substituted with one or more groups such as —$OR^1$ groups, where $R^1$ is selected from H, ($C_1$-$C_6$)alkyl, ($C_1$-$C_6$) aryl, and ($C_6$-$C_{14}$)aryl-($C_1$-$C_6$)alkyl groups.

In some embodiments, the polymer can include an amphiphilic block copolymer. In additional specific embodiments, the polymer can include a copolymer of lactic acid and glycolic acid (e.g., PLGA). In additional specific embodiments, the polymer can include at least one of PLGA-block-PEG and PLGA.

In some embodiments, the surface of the microspheres can be hydrophilic (e.g., the microspheres can include a PLGA core and a PLGA-block-PEG surface). In such embodiments, the liquid carrier vehicle can be hydrophilic. In some embodiments wherein the surface of the microspheres are hydrophilic and the liquid carrier vehicle is hydrophilic, the resulting injectable compositions can be configured for injection into biological tissue such as fatty tissue, an epidural space, etc.

In specific embodiments, the PLGA-block-PEG surface can be poly(D,L-lactide-co-glycolide)-co-polyethylene glycol (e.g., with a ratio of lactic acid to glycolic acid of from about 50:50 to about 95:5 or with a ratio of lactic acid to glycolic acid of about 85:15).

In some embodiments, block copolymers of PLGA and PEG are contemplated herein, wherein the PEG block can have a molecular weight of from about 500 Da to about 40,000 Da (e.g., from about 1,000 Da to about 20,000 Da; or about 2,000 Da to about 10,000 Da. While not wishing to be bound by any specific theory, it is believed that when a PEG-containing block copolymer is used to make the microspheres of the various embodiments described herein, the PEG-containing blocks tend to migrate toward the surface of the microspheres, thereby making the surfaces of such microspheres relatively more hydrophilic.

Alternatively, in some embodiments, the surface of the microspheres can be hydrophobic. In such embodiments, the liquid carrier vehicle can be hydrophobic, and the polymer can include PLGA. Additionally, in some embodiments wherein the surface of the microspheres are hydrophobic, and the liquid carrier vehicle is hydrophobic, then the injectable compositions can be configured for injection into a biological tissue such as a joint, the synovial cavity of a joint, nerves, an eye, or surrounding tissue, the vitreous body of an eye or surrounding tissue, etc.

The microspheres include an active pharmaceutical ingredient and polymer. The core of the microspheres can include an API (e.g., dexamethasone acetate), which has relatively poor water-solubility, and polymer (e.g., poly(lactide-co-glycolide (PLGA)): and the surface of the microsphere can comprise a second polymer (e.g., PLGA-co-polyethyleneglycol block copolymer, wherein the PEG block can be distal to the surface of the microsphere).

In some embodiments, the surface of the microsphere can also include a specified amount of API that is soluble in the vehicle, the amount of which may be optimized to control burst release of the drug. It can be desirable to have an initial bolus dose of drug, followed by sustained release of the API(s) from the microspheres at a controlled rate over time. U.S. Pat. No. 7,758,778, which is incorporated by reference as if fully set forth herein, describes methods for preparing microsphere formulations containing pharmaceutically active agents.

The surface of the microspheres can be selected or modified through functionalization so that the surface can be soluble or miscible in the delivery vehicle: or insoluble or immiscible in the targeted physiological injection site. In general, microspheres incorporating pharmaceutical or pharmacological agents and surface modification of the particles can be prepared by methods known in the art. See, for example, Published U.S. Patent Application No. 2003/0099682, and U.S. Pat. No. 6,497,729, both of which are incorporated by reference as if fully set forth herein. Other suitable synthetic methods known in the art can be employed.

The selection and/or modification through functionalization of the surface of the microspheres can provide a stable, homogeneous injection suspension; can minimize precipitation or settling of the microspheres; can improve performance when administering the injection solution; and/or can allow a practitioner to reliably administer an effective dose of the pharmacological agent. At the same time, the immiscibility between the injection solution or suspension and the targeted physiological injection site can provide the capability for the microspheres to agglomerate at the injection site and not within the injection vehicle, as described herein.

In some embodiments, the microsphere surface can include a substantially polar, water-miscible, or water-soluble material. In alternative embodiments, the microsphere surface includes a substantially non-polar, water-immiscible, or water-insoluble material.

In general, and without wishing to be bound by theory, it is believed that when a carrier vehicle (e.g., an aqueous phase) containing suspended microspheres is injected into a biological environment having substantially different hydrophilicity or hydrophobicity than the suspension or solution itself, the vehicle will form a separate phase with respect to the environment. In some embodiments, the microspheres and vehicle will form a depot. Over time, the vehicle will be absorbed by the body, while the microspheres will remain substantially localized at the injection site. Eventually, the vehicle will be substantially absorbed by the body, leaving a localized, agglomerated concentration of the microspheres at or substantially near the injection area. As the microspheres degrade over time, and through diffusion processes, the API(s) contained therein can be released into the immediate anatomical surroundings, providing localized delivery of an API.

As is described in the art, accidental injection of a microspheres into an unintended anatomy can pose serious health risks for the patient. Injection of particulate matter into an artery can result in blocking or obstruction of the artery, arterioles or capillaries, resulting in damage to tissue relying on the blood supplied by the blocked vasculature. This is particularly true for biodegradable microspheres having a size dimension greater than about 10 µm, since the microspheres cannot pass easily through capillary beds. Accordingly, in some embodiments, the microspheres of the various embodiments described herein have no dimension greater than about 10 µm (e.g., no dimension great than about 0.1 µm to about 10 µm; about 0.25 µm to about 9 µm; about 0.5 µm to about 8 µm; or about 1 µm to about 7 µm). In some embodiments, the microspheres of the various embodiments described herein are substantially spherical, such that they have a circularity value of from about 0.5 to about 1:about 0.8 to about 0.99; about 0.85 to about 1; or about 0.90 to about 0.99 as determined using a Malvem Morphologi G3 instrument. In some embodiments the microspheres can have a D90[num] circularity value of from about 0.90 to about 1.0 (e.g., from about 0.93 to about 0.99; about 0.95 to about 0.99; about 0.90 to about 0.99; or about 0.95 to about 1.0). In some embodiments the microspheres can have a D90[num] circularity value of from about 0.5 to about 1.0 (e.g., from about 0.8 to about 0.99:about 0.8 to about 1:about 0.85 to about 1; or about 0.90 to about 0.99).

The microspheres employed herein have a suitable and appropriate dimension. In some examples, the microspheres can be oval, spherical, elliptical, tubular, etc. In addition to the shape, the microspheres will have a suitable size. In addition, the microspheres will have a particle size distribution, which can be quantified by a "D value." The term "D50," as used herein refers, to the 50th percentile number- or volume-based median particle diameter, which is the diameter below which 50% by number or volume of the particle population is found. Other percentages such as D10 (10%), D90 (90%), D99 and D100 (100%) are also commonly used. The term "D99," as used herein, refers to the 99th percentile of either a number- or volume-based median particle diameter, which is the diameter below which 99% by number of volume of the particle population is found. The number or volume measurement is indicated by [num] for number or [vol] for volume.

The microspheres of the various embodiments described herein can have a D50[num] particle diameter of less than about 5 µm (e.g., a D50[num] particle diameter of about 1 µm to about 5 µm; about 1.5 to about 4 µm; about 1.75 to about 3.5 µm; or about 2 to about 3 µm). In other embodiments, the microspheres can have a D90[num] particle diameter of less than about 9 µm (e.g., a D90[num] particle diameter of about 2 µm to about 9 µm; about 3 µm to about 7 µm; or about 3.5 µm to about 6 µm). In still other embodiments, the microspheres can have a D99[num] particle diameter of less than about 10 µm (e.g., D99[num] particle diameter of about 3 µm to about 10 µm; about 4 µm to about 9 µm; about 4.5 to about 8 µm; or about 5 µm to about 7 µm). In other embodiments, the microspheres have a D100[num] particle diameter of less than about 15 µm (e.g., a D100[num] particle diameter of about 3 µm to about 12 µm, about 4 µm to about 11 µm; or about 5 µm to about 10 µm.

Particle diameters and particle size distributions can be determined by single particle optical sizing (SPOS) as described, for example, in U.S. Pat. No. 9,423,335, which is incorporated by reference as if fully set forth herein. Other methods for determining particle diameters and particle size distributions can also be used, including SEM, microscopy, light scattering, laser diffraction, coulter counter (electrical zone sensing), and digital image analysis.

The microspheres of the various embodiments described herein will have, in some embodiments, low porosity. The level of porosity can, in some cases, be determined using SEM. While not wishing to be bound by any specific theory, it is believed that low porosity microspheres can be beneficial because such microspheres can exhibit, among other features, controlled burst and sustained release of the APIs contained therein.

The microspheres of the various embodiments described herein will have a density. In some embodiments, the density is from about 0.5 to about 2 g/cc$^3$ (e.g., from about 0.5 to about 1.5 g/cc$^3$; about 0.75 g/cc$^3$ to about 1.5 g/cc$^3$; and about 1.0 g/cc$^3$ to about 1.5 g/cc$^3$).

In general, the pharmaceutical compositions and methods described herein comprise microspheres having that are well-suited for injecting in and around vascular tissue where occlusion of downstream arteries, arterioles, and capillaries can yield serious negative consequences including, but not limited to, infarct if a practitioner accidently injects the pharmaceutical composition into the vascular tissue. This advantage is provided at least in part by the microspheres' size, such that even if the microspheres are accidently introduced into a blood supply, they can pass through the capillary bed without causing obstruction. See, e.g., Published U.S. Patent Application No. 2001/0012522, which is incorporated by reference as if fully set forth herein. Thus, the risk of spinal cord infarct resulting from accidental injection outside of the target injection area (e.g., the epidural space), or into arteries that pass through the epidural space can be reduced.

In some embodiments, the microspheres are biodegradable. In additional embodiments, the microspheres are bioerodible. In additional embodiments, the microspheres are biocompatible.

The microspheres can be present in any suitable and appropriate concentration, in the injectable compositions of the various embodiments described herein, so long as the injectable compositions of the various embodiments described herein are still flowable and injectable. It should be understood, however, that a certain composition will ultimately cease to be injectable when a specific concentration of solids is reached. In specific embodiments, the microspheres can be present in a concentration of about 1 mg/mL to about 500 mg/mL in the vehicle (e.g., from about 50 mg/mL to about 250 mg/mL; about 100 mg/mL to about 500 mg/mL; about 10 mg/mL to about 300 mg/mL: or about 1 mg/mL to about 200 mg/mL).

Any suitable active pharmaceutical ingredient (API), or combinations of two or more APIs, can be incorporated into the microspheres of the various embodiments described herein, provided the resulting injectable compositions retain their chemical and physical stability, as well as requisite biological activity, over the extended periods of time associated with the manufacture, shipping and storage of the product, as generally described herein. In some embodiments, the injectable compositions can comprise additional APIs (e.g., local anesthetics, such as lidocaine, ropivacaine, mepivacaine, cocaine, procaine, and lidocaine) that are comprised in the injectable compositions, and can be the same or different as the API(s) comprised in the microspheres.

Combinations of microspheres, within an injectable composition, comprising different APIs are also contemplated herein. Thus, for example, a plurality of microspheres comprising one API (e.g., dexamethasone) and a second (third, fourth or more) plurality microspheres can comprise a second API (bupivacaine), such that two APIs can be delivered at the same time, at the same site, but in different microspheres.

Suitable APIs, whether incorporated into the microspheres and/or into the injectable compositions, separate from the microspheres (e.g., dissolved in the vehicle), are disclosed in the Merck Index (14th Ed.) and the USP Dictionary (2011), for example. The selection of specific (or class) of API will typically depend on, among other things, the underlying disease or disorder to be treated. Examples of general classes of APIs that are contemplated herein include APIs used to/for treat back pain (e.g., lumbar, dorsal, ventral, thoracic, and/or cervical) (e.g., opioids such as codeine, oxycodone, hydrocodone, and morphine); epidural injections; local nerve block therapy; treat ankylosing spondylosis (e.g., non-steroidal anti-inflammatory drugs (NSAIDS) including ibuprofen; flurbiprofen, naproxen and naproxen sodium; diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, COX-2 specific inhibitors such as celecoxib, valdecoxib, lumiracoxib and/or etoricoxib; and disease modifying anti-rheumatic drugs (DMARDS), including sulfasalazine, methotrexate, lefluonomide, hydroxycholoquine, corticosteroids (e.g., triamcinolone and esters thereof; methylprednisolone and esters thereof; dexamethasone and esters thereof; betamethasone and esters thereof; cortivazol and related compounds, difluprednate; and cortisone), abatacept adalimumab, anakinra, certolizumab, etanercept, golimumab, infliximab, rituximab, tocilizumab, and tofacitinib; treat inflammation (e.g., NSAIDS); treat epilepsy, neuropathic pain, hot flashes or restless leg syndrome (e.g., gabapentin); treat multiple sclerosis (e.g., glatiramer acetate); promote wound healing (e.g., phenytoin; misoprostol; and metronidazole); treat vasospasm for the brain and cerebrospinal fluid (e.g., calcium channel blockers, such as nimodipine, nicardipine, and vermapil; rho kinase inhibitors, such as fasudil; statins; hormones, such as erythropoietin and estrogen; phosphodiesterase inhibitors, such as milrinone, papaverine, and cilostazol; endothelin-1 antagonists, such as clazosentan; and heparin), treat myofascial gravis (e.g., azathioprine and mycophenolate); treat joint pain; treat gout (e.g., xanthine oxidase inhibitors, including allopurinol and febuxostat); treat rheumatoid arthritis (e.g., NSAIDs, DMARDs, and corticosteroids); treat trigeminal neuralgia (e.g., anticonvulsants including carbamazepine, oxcarbazepine, lamotrigine, and phenytoin; antispasmodics including baclofen; and onabotulinumtoxin A); treat migraine or cluster headaches (e.g., almotriptan, alperopride, amitriptyline, amoxapine, atenolol, clonidine, codeine, coproxamol, cyproheptadine, dextropropoxypene, dihydroergotamine, diltiazem, doxepin, ergotamine, eletriptan, fluoxetine, frovatriptan, isometheptene, lidocaine, lisinopril, lisuride, loxapine, methysergide, metoclopramide, metoprolol, nadolol, naratriptan, nortriptyline, oxycodone, paroxetine, pizotifen, pizotyline, prochlorperazine propanolol, propoxyphene, protriptyline, rizatriptan, sertraline, sumatriptan, timolol, tolfenamic acid, tramadol, verapamil, zolmitriptan, and non-steroidal anti-inflammatory drugs); and treat headache (e.g., aspirin, paracetamol, naproxen, and ibuprofen).

In some embodiments, the microspheres of the various embodiments described herein comprise one or more corticosteroids. In some embodiments, the microspheres of the various embodiments described herein comprise two corticosteroids. In some examples, the two corticosteroids have different rates of diffusion from the microspheres into surrounding tissue.

In other embodiments, the microspheres of the various embodiments described herein comprise a corticosteroid in combination with an API used to treat neuropathic pain, such as gabapentin. In some embodiments, the API used to treat neuropathic pain can be comprised in at least one of the microspheres and the injectable composition, as a separate component of the injectable composition.

The APIs contemplated herein can be in any suitable forms including as prodrugs, hydrates, clathrates, or solvates.

One specific class of APIs that can be employed includes anti-inflammatory agents, for example, synthetic, glucocorticoid steroids. Within the synthetic, glucocorticoid steroids, a specific API that can be employed is dexamethasone and esters thereof (e.g., dexamethasone acetate, also known as 9 alpha-fluoro-11-beta, 17-alpha, 21-trihydroxy-16 alpha-methylpregna-1,4-diene-3,20-dione 21-acetate).

Another API that can be employed includes corticosteroids such as betamethasone and esters thereof (e.g. betamethasone valerate, betamethasone dipropionate, and polyfluorinated corticosteroids such as difluprednate).

Use of dexamethasone acetate as an anti-inflammatory agent can be advantageous in specific embodiments. Dexamethasone acetate has a relatively low water-solubility, which facilitates sustained drug delivery from the microspheres of the various embodiments described herein. Additionally, the drug has been shown to be a relatively potent corticosteroid that does not reduce water content of neural tissue.

Dexamethasone and its esters (i.e. dexamethasone acetate) has higher anti-inflammatory potency than many other corticosteroids, which may reduce the number of doses or concentration of dose needed to treat the patient. Dexamethasone acetate also has low water solubility, <0.15 mg/mL, which can be preferred for formulation of a sustained-release dosage form. As diffusion and polymer degradation are two main mechanisms of drug release from biodegradable microspheres, a pharmacological agent having lower water solubility may elute at a slower rate from the microspheres compared to other agents with high water solubility. Furthermore, dexamethasone acetate has been shown to achieve an anti-inflammatory effect in the brain without reducing tissue water content. See, e.g., H. James, "Effects of Steroids on Behavior, Electrophysiology, Water Content and Intracranial Pressure in Cerebral Cytotoxic Edema," Pharmacology Biochemistry and Behavior, Vol. 9, pp. 653-657, 1978. Thus, in specific embodiments, it can be advantageous to choose dexamethasone acetate for treatment of low back pain to avoid reduction in water content of the targeted nerve roots.

While not wishing to be bound by any specific theory, the use of a corticosteroid in combination with another API can be advantageous because the corticosteroid can reduce the foreign body response or inflammatory response to the presence of the microspheres of the various embodiments described herein.

Selection of the API will depend in part upon the underlying disease or disorder to be treated. In specific embodiments where the API is an anti-inflammatory agent, for example, a synthetic, glucocorticoid steroid, such as dexamethasone acetate, the disease or disorder to be treated can include at least one of: pain, chronic pain, mild pain, moderate pain, severe pain, acute pain, neuropathic pain, lower back pain, sciatica, radiculopathy, lumbar radiculopathy and lumbosacral radiculopathy. In some embodiments, the API is dexamethasone acetate comprised in extended-release microspheres intended for lumbar transforaminal epidural injection and indicated for treatment of lumbar radiculopathy (radiating pain). The microspheres are administered as a micro-suspension in a vehicle.

In other embodiments, for example, the API can be administered via an intravitreal injection into the eye. For such an administration, the composition can be employed to treat, e.g., macular degeneration or diabetic macular edema. APIs suitable for the treatment of such diseases or disorders are disclosed, e.g., in the Merck Index (14th Ed.) and the USP Dictionary (2011). For example, in embodiments where the composition is employed to treat diabetic macular edema, via an intravitreal injection into the eye, the API can include dexamethasone acetate.

The API can be present in the injectable compositions in any suitable and appropriate amount. For example, the API can be present in the injectable compositions in an amount such that the resulting injectable compositions retains its chemical and physical stability, as well as requisite biological activity, over the extended periods of time associated with the manufacture, shipping and storage of the product.

In specific embodiments, it may be desirable to maximize, or increase, the amount of API present, relative to the total amount of injectable compositions. In such embodiments, it may be desirable to employ an injectable composition having a relatively low volume, for patient safety, compliance, and comfort purposes.

As such, in specific embodiments, the active pharmaceutical ingredient can be present in a weight of up to about 50 wt. % of the polymer (e.g., from about 5 wt. % to about 50 wt. %; about 10 wt. % to about 40 wt. %; about 15 wt. % to about 35 wt. %:about 20 wt. % to about 35 wt. %; or about 20 wt. % to about 40 wt. % of the polymer). The polymer comprising the API is used to produce the microspheres of the various embodiments described herein. In some embodiments, microspheres can be produced from such a polymer to give microspheres having high API loading and that still exhibit controlled burst and sustained release. In further specific embodiments, the active pharmaceutical ingredient can be present in a weight of up to about 40 wt. % of the polymer. In alternative specific embodiments, the active pharmaceutical ingredient can be present in a weight of at least about 10 wt. % of the polymer. In further specific embodiments, the active pharmaceutical ingredient can be present in a weight of at least about 20 wt. % of the polymer. In alternative specific embodiments, the active pharmaceutical ingredient can be present in a weight of about 20 to about 35 wt. % of the polymer or about 20 to about 40 wt. % of the polymer.

In some embodiments, the active pharmaceutical ingredient can be present in a weight of up to about 50 wt. % of a plurality of microspheres (e.g., from about 5 wt. % to about 50 wt. %; about 10 wt. % to about 40 wt. %; or about 15 wt. % to about 30 wt. % of a plurality of microspheres), wherein the weight percent is adjusted to account for the presence of lyoprotectant or other materials that may be present on the surface of microspheres in the plurality of microspheres.

The specific amount (measured in units of mass) of the API(s) employed in the injectable compositions will typically depend, for example, on the amount of composition to be delivered. The amount of composition to be delivered will typically depend, for example, on the size, weight, age and health condition of the patient, the disease or disorder to be treated, the location or site of administration, the duration of drug release, potency of the API(s) as well as the specific API employed.

Some embodiments are directed to kits including all of the desired tools, solutions, compounds, including mixing vessels, utensils, and injection devices, to treat a patient according to any of the methods described herein. In one embodiment, a kit includes microspheres of the various embodiments described herein. The microspheres can be sterile-packaged as a dry powder in a suitable container (e.g., a substantially water-impermeable) such as a syringe, vial (e.g., the vial can include a septum and/or a crimp seal; and the vial can optionally comprise an inert atmosphere, such as a nitrogen atmosphere or dry air) or pouch (e.g., a pouch comprising a moisture barrier; and the pouch can optionally comprise an inert atmosphere, such as a nitrogen atmosphere, or dry air). The kit can also include a desiccant. The desiccant can be included in the pouch or integrated into the layers of the pouch material. In some embodiments, the microspheres can be sterile-packaged in frozen vehicle. As mentioned previously, the vehicle can be any suitable vehicle, including flowable vehicles (e.g., a liquid vehicle) such as a flowable, bioresorbable polymer, saline, sterile water, Ringers solutions, and isotonic sodium chloride solutions. Examples of vehicles include, but are not limited to, Sodium Chloride Injection USP (0.9%), Ringers Injection USP, Lactated Ringers Injection USP, Sodium Lactate Injection USP, Dextrose Injection USP (5% or 10%). Bacteriostatic Water for Injection USP and Sterile Water for Injection USP. In some examples, the microspheres can be suspended in water; pre-filled into a container, such as a syringe; and frozen.

The kit can include at least one static mixing element, such as a one that is attached to a syringe. In some embodiments, the user provides a static mixing element to deliver the microspheres.

The kit can also include beads that serve to, among other things, disaggregate any microsphere agglomeration that can occur when the microspheres of the various embodiments described herein are reconstituted with a vehicle. In some embodiments, the beads are sufficiently larger than the microspheres, so that the microspheres can be selectively delivered to the injection site, while the beads remain in the injection device (e.g., a syringe). For example, the beads can have at least one dimension that is about 1 mm. The beads can be of any suitable shape, including spherical and oval in shape. The beads can also have any suitable texture. For example, the beads can have a smooth texture and/or a rough texture. The beads can also be made of any suitable material, including glass, ceramic, metal (e.g. stainless steel), polymeric (e.g. ePTFE or polypropylene), and composite materials. The beads can be included in the kit in a separate container; in the same container as the microspheres of the various embodiments described herein; or the user can provide beads of suitable size, shape, texture, and/or materials at the point of care.

The kit can also include an injection vehicle described herein, such as sterile water or sterile saline (e.g., in the case where the target injection area is substantially hydrophobic or lipophilic) or other suitable vehicle, including a non-aqueous vehicle (e.g., a hydrophobic, liquid vehicle described herein). Prior to administration, the microspheres can be added to the injection vehicle to form a suspension and agitated (e.g., stirred, shaken or vortexed) to maximize homogeneity. In some embodiments, the microspheres can come in the kit, suspended in a vehicle, such as a non-aqueous vehicle (e.g., a hydrophobic, liquid vehicle described herein).

The kit can further include a hypodermic needle or other delivery device, such as a cannula, catheter or other suitable tubing. The kit can further include instructions, dosage tables, and other pertinent information for a practitioner.

The kit can include one or more additional APIs (e.g., a local anesthetic) either in the same container as the microspheres of the various embodiments described herein or in a separate container, such that the API in a separate container can be combined with the microspheres and vehicle to provide a bolus of an API upon administration (e.g., injection) of the microspheres. In other embodiments, the user can provide one or more additional APIs that can be combined with the microspheres of the various embodiments described herein, at the point of care. In one specific example, a kit comprises PLGA microspheres comprising dexamethasone acetate and a powder comprising dexamethasone sodium phosphate. The PLGA microspheres and the powder are, in some embodiments, reconstituted with a suitable vehicle (e.g., sterile saline or water) that suspends the PLGA microspheres and dissolves the powder.

The kits will include instructions or printed indicia, to provide for directions for reconstituting the contents of the multiple packages, and/or for the administration of the resulting composition (e.g., the injectable compositions). For example, instructions on printed indicia can instruct injection into biological tissue including at least one of fatty tissue, epidural tissue, and at or near a targeted nerve.

The microspheres described herein can be stored, e.g., as a lyophilized powder in a sealed, dry container. Prior to injection, the particles can be mixed with an injection vehicle, and an aliquot of the resulting suspension can be collected for injection into the patient. In typical settings, this procedure can be done by drawing the suspension into a needle for subcutaneous injection. However, other methods of delivering the suspension to a desired injection can be used. In one embodiment, a 22 gauge, 3.5 inch Quincke spinal needle can be used. In another embodiment, a Touhy needle can be used. Other methods will be apparent to those skilled in the art and are dependent on the location of the intended injection. See, e.g., Cohen et al, "Randomized. Double-blind, Placebo-controlled. Dose Response, and Pre-clinical Safety Study of Transforaminal Epidural Etanercept for the treatment of Sciatica," *Anesthesiology* 110-1116-1126 (2009), which is incorporated by reference as if fully set forth herein.

One problem with existing microsphere formulations is settling of the microspheres in the delivery vehicle, which can affect patient dosing. A uniform, but unstable suspension of biodegradable microspheres can be achieved, in prior art systems and methods, by mixing or stirring the microspheres into the delivery vehicle. It then becomes necessary, in most cases, to immediately load the suspension into the delivery device (e.g. a hypodermic needle) immediately after mixing since the microspheres will begin to settle after a period of time. The concentration of microspheres in the suspension can vary using this type of approach, since the amount of time between mixing, needle loading, and injection depend on the practitioner-dependent variables.

In contrast, advantages of the invention include the use of a microsphere/delivery vehicle suspension that has a high degree of stability, thus providing the capability to perform accurate dosing without placing impractical or inconvenient limits of the time between mixing and loading the delivery device on the practitioner.

The injectable compositions described herein can be formulated for administration, via injection, to a subject (e.g., a human or animal subject).

As described herein, the injectable compositions can be formulated to provide a desired or requisite rate of release of the API. In specific embodiments, the injectable compositions can have a substantially first order release profile. In alternative specific embodiments, the injectable compositions can have a substantially zero order release profile.

Depending upon the selection of polymer, microsphere. API, etc., the API can be released into the target injection site area over a specified period of time. For example, the polymer, microsphere, and API(s) can independently be selected for release of the API into the target injection area over a period of days, weeks, or months. This process can occur by, e.g., diffusion of the API out of the microspheres; or by the microspheres dissolving or decomposing over time, which can release the API into the injection site. In one embodiment, the microspheres are capable of releasing the API over selectable periods ranging from about 14 days to about 170 days. Thus, a patient can receive substantially-continual dosing of the API over extended periods, if desired, which can reduce the need to receive repeated injection treatments.

The injectable compositions described herein can be formulated for administration, via injection, to a mammal (e.g., human), over a suitable, appropriate and effective period of time. In specific embodiments, the administration can be carried out no more than once per about 14 days. In additional specific embodiments, the administration can be carried out no more than once per about 42 days or no more than once per about 56 days. In additional specific embodiments, the administration can be carried out no more than once per about 84 days. In additional specific embodiments, the administration can be carried out no more than once per about 126 days. In additional specific embodiments, the administration can be carried out no more than once per about 170 days.

In specific embodiments, the administration is carried out with fluoroscopy. In alternative specific embodiments, the administration is carried out without fluoroscopy.

In specific embodiments, the administration is carried out with ultrasound. In alternative specific embodiments, the administration is carried out without ultrasound.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Examples

The following illustrative examples are provided to facilitate testing, determine effective dosing, and describe preferred methods for use of the pharmaceutical compositions described herein. The examples below are non-limiting with respect to the claims.

Materials and Methods

The microspheres, and compositions comprising those microspheres, of the various embodiments described herein are analyzed using USP methods known in the art to determine, among other things, the pH of the compositions, the in vitro release of API, and the impurities present. Table 1, below, shows the various methods used to analyze the microspheres, and compositions comprising those microspheres, of the various embodiments described herein.

TABLE 1

| | |
|---|---|
| pH | USP <791> |
| Identification (HPLC) Dexamethasone Acetate | USP <621> |
| ID PLGA | USP <197> |
| In Vitro Retease (IVR) | USP <711>, acceptance Table 2 |
| Water Content | USP <921> |
| Content Uniformity | USP <905> |
| Impurities | USP <621>; see also Dexamethasone Acetate USP Monograph |
| Residual Solvent | USP <467> by GC |
| Sterility | USP <71>| |
| Bacterial Endotoxins (LAL) | Biological, USP<85> Gel Clot method or LAL method |
| Trace Metals | USP <233> |

Particle size distribution of the various microsphere formulations can be determined by single particle optical sizing (SPOS) and characterized by scanning electron microscopy. The stability of a suspension of microspheres within a carrier vehicle can be determined by observing settling times. These data can be confirmed by assaying aliquots from top, middle, and bottom locations of the suspension at selected time intervals, e.g., 1 hour, 2 hours, 8 hours, etc.

Polymer Degradation Studies

To prepare the microspheres, an organic phase containing ethyl acetate, dexamethasone acetate, PLGA and PLGA-PEG was made. The aqueous phase was a 1% PVA solution in water. The aqueous and organic phases were pumped together through a static mixer at set flow rates to create the emulsion. Hardening water joined the static mixer to harden the microspheres. The microspheres were prepared using a continuous batch system. Once concentrated, a few drops of suspension were removed from the collection vessel to measure particle size. Equal volumes of USP water were added to the collection vessel and the particle batch will be concentrated again to the original volume of the concentrate. This step was repeated three times. Final particle size and solids content was measured. Prior to lyophilization, 10% w/w of NaCl was added to the suspension based on the results of solids content. The batch was then transferred to SS plates (100 mL volume per plate) and lyophilized to dryness.

Particle sizes of the samples were measured using Accu-sizer 780 SIS (Particle Sizing System). Particles were measured in extinction mode with size threshold of 1.5 μm. For particles in suspension: Suspension was diluted with USP water to achieve a concentration of 4,000 to 9,000 particles/mL.

Precipitation titration was used to measure the salt content in the samples.

Polymer molecular weight was measured using gel permeation chromatography (GPC). The samples were analyzed in three PLgel MIXED-C columns at 30° C. using THF as a solvent running at the flow rate of 1 mL/min. A 100 μL injection volume of sample was used with a run time of 45 minutes. The molecular weight calculations were based on polystyrene standards that were analyzed on the same date, with no corrections for differences between polystyrene and the samples. A negative control of THF sample was also analyzed to confirm the baseline response, especially at lower molecular weights.

Buffer used for degradation contained 0.05% Tween-80 in ⅟₃₀ M phosphate buffer (pH 7.0). For each test batch, 30 sets (3 tubes×10 time points) of 100 mg particles were suspended in 5 mL of buffer in 15 mL polypropylene tubes or glass scintillation vials. These tubes were incubated at 37° C. incubator. At each time point, 3 tubes of particles were removed from 37° C. incubator, centrifuged at 3500 rpm for 20 minutes or until the supernatant was clear, and buffer was decanted. Prior to analysis, all samples were dissolved in tetrahydrofuran (THF) to a concentration of approximately 4 mg/g and filtered through 0.2 micron PTFE filters. Time points for the in-vitro sample analysis were as follows: 0, 10, 20, 30, 50, 90, 120, 180 and 220 days from the start date of the study.

Microsphere Preparation and Testing of Dosage Forms

Procedure [A1]: Microsphere Having a Hydrophilic Surface Created by Block Copolymer—Aqueous Vehicle In this example, microspheres containing an active API can be prepared using the following oil-in-water emulsion technique. First, an organic phase can be prepared by dissolving an API and a suitable polymer (e.g., PEG-block-PLGA, such as mPEG 5000 initiated PLGA with 75/25 lactic acid/glycolic acid molar ratio) in a suitable organic solvent (optionally pre-filtered to remove particulates), such as ethyl acetate, chloroform, dichloromethane, tetrahydrofuran or combinations of two or more solvents. In some embodiments, the concentration of the polymer and/or the API in the organic solvent can be from about 1 wt. % to about 10 wt. %. In some embodiments, the organic solvent can be saturated with the API and/or the polymer. In some embodiments, a surfactant is used. An aqueous phase can be prepared by dissolving a suitable surfactant (e.g., a surfactant disclosed herein, such as hydrolyzed polyvinyl alcohol (PVA)) in water (e.g., deionized water, optionally pre-filtered to remove particulates). The water (e.g., deionized water) can be, in some embodiments, saturated with the organic solvent.

In some embodiments, the total concentration of solids in the organic phase and/or the aqueous phase can be about 0.25 to about 40% (e.g., about 0.75% to about 25%; about 1% to about 20%; or about 1.5% to about 15%).

Next, the organic phase can be added to the aqueous phase and an emulsion can be formed (e.g., by agitating with a high-shear rotary immersion mixer). The ratio of the aqueous phase to the organic phase can be from about 1:1 to about 6:1. In some embodiments, the organic phase and/or the aqueous phase can be filtered to remove any particulates.

The resulting oil-in-water emulsion can be further processed through a high-shear microfluidizer to reduce the oil droplet size, then stirred to allow the hydrophilic portions of the polymer (e.g., PEG chains) to orientate to the oil droplet surface. The resulting emulsion can be added to an excess of water (e.g., deionized water or water comprising a salt, such as sodium chloride) and continuously agitated to harden the polymeric microspheres. Next, after about 60 minutes, the resulting microspheres can be progressively isolated through 50 μm, 10 μm, and 1 μm filters, optionally under positive pressure. The particles collected on the 1 μm filter can be washed with water (e.g., deionized water) and with any other suitable solvents. In some embodiments, the particles are washed so as to substantially remove any surfactant that remains form the emulsion technique.

In some embodiments, the microspheres can be resuspended in water and centrifuged prior to lyophilization (e.g., centrifuged at 1500 G forces for 4 minutes). The centrifugation can be performed one or more times so as to remove residual surfactant. Without wishing to be bound by any specific theory, it is believed that removal of surfactant can help reduce agglomeration of microspheres before, during, and/or after administration to a subject (e.g., a human or animal subject).

In some embodiments, the microspheres are lyophilized to dry them, optionally in the presence of a lyoprotectant.

In some embodiments, the microspheres are jet-milled. The dried (i.e. lyophilized) microspheres are fed into the mill at a controlled feed rate. Inside the mill, the microspheres are contacted with a high pressure, dry air stream at high velocity accelerating the aggregated particles. The collisions between any aggregated microspheres result in disaggregation. The jet mill injection pressure and microsphere feed rate can be selected so that the microspheres are disaggregated, but not damaged or otherwise altered by the milling process. The dry air and microspheres exit the jet mill where a cyclone can be used to recover the jet-milled microspheres from the exhaust stream. The jet-milled microspheres are packaged and stored in sealed containers (e.g., a vial or pouch) under refrigeration, under an inert atmosphere, and/or under a low-moisture atmosphere. Sealed vials can be gamma irradiated prior to analysis or administration.

In some embodiments, some or all of the steps described herein (e.g., including the packaging step) can be performed at room temperature or at reduced temperatures (e.g., at a temperature of from about −25° C. to about 15° C.; from about −10° C. to about 10° C.: or from about 1° C. to about 8° C.

Microspheres prepared according to Procedure [A1] can be predicted to have an average diameter of about 2 µm and a maximum diameter of about 10 µm.

Procedure [A2]: Microsphere Having a Hydrophilic Surface Created by Block Copolymer—Aqueous Vehicle One alternative approach includes the steps of Procedure A1, but, when the polymer is PEG-block-PLGA, additional PLGA can be added to the organic phase to reduce the overall PEG content of the resulting microsphere.

Procedure [A3]: Microsphere Having a Hydrophilic Surface Created by Block Copolymer—Aqueous Vehicle One alternative approach includes the steps of Procedure [A1], but the emulsion is not microfluidized, and the hardened microspheres can be progressively isolated through 100 µm and 20 µm filters.

Without wishing to be bound by theory, it is believed that when the polymer is PEG-block-PLGA, the block copolymer PEG-co-PLGA may associate with several surfaces or interfaces: a) the surface of the organic phase droplets in the emulsion acting as a surfactant; b) the hydrophobic blocks with the organic phase; and c) the hydrophilic PEG blocks with the surrounding aqueous phase. Upon hardening, the surface of the microspheres may include PEG-co-PLGA on the surface.

Microspheres prepared according to Procedure [A1] can be predicted to have an average diameter of about 2 µm and a maximum diameter of about 10 µm. Microspheres prepared according to Procedure [A3] herein can be predicted to have an average diameter of about 40 µm and a maximum diameter of about 100 µm.

In general, without wishing to be bound by theory, the percent-by-weight (% weight) of active API contained within microspheres prepared by the methods described herein can be approximately equal to, or slightly less than the % weight of the agent with respect to the oil-phase polymer. In the examples presented herein, if the API is dexamethasone acetate, the dexamethasone acetate can be estimated to be 25% by weight of the microsphere. It will be understood that the amount of API contained in the microsphere can be adjusted by varying the drug to polymer ratio in the oil phase. In addition, the API may be incorporated into the organic phase as a suspension if a solvent is used that solubilizes the polymer, but not the agent.

Microspheres prepared according to the methods described herein steps can be expected to form a stable suspension in water over a reasonable range of solid content, e.g., 1-30% weight/volume. Such suspension can be stable for greater than 2 hours, which is typically long enough to enable a physician or other practitioner to form and administer the suspension into a patient.

Without wishing to be bound by theory, it can be reasonably expected that dexamethasone acetate will release continuously over about 84 days in vitro, with about 20% of the drug released in 3 days, 50% in 25 days, and 90% in 60 days. It will be understood that the release profile may be adjusted by one or more of the following, including combinations: increasing or decreasing drug to polymer ratio; increasing or decreasing polymer molecular weight; increasing or decreasing particle size; increasing or decreasing polymer degradation time (by decreasing or increasing glycolic acid content); or increasing or decreasing hydrophilicity of microsphere surface.

Procedure [AX] Microspheres Having a Hydrophilic Surface—Aqueous Vehicle

Microspheres can be prepared by an oil-in-water emulsion technique. An organic phase can be prepared by dissolving between 2% and 4% weight/volume dexamethasone acetate, between 3 and 8% weight/volume poly-lactic-co-glycolic acid, and between 0.05 and 0.5% weight polyethylene glycol-block-poly-lactic-co-cycolic acid in ethyl acetate. An aqueous phase can be prepared by dissolving between 0.1 and 4% polyvinyl alcohol in sterile purified water. The aqueous and water phases can be combined in a tee fitting using metering pumps for both fluids at ratios between 5:1 and 1.25:1. The effluent from the tee can be emulsified by passing the mixture through a static mixer. The emulsion can be further mixed with purified water having a temperature between 0° C. and 15° C. and the mixture run through a tubing system to harden the microspheres. The tubing system can optionally be sized to produce a flow with a Reynolds number between 1000 and 12000 and to have sufficient space time to harden the microspheres, which can be on the order of 30 to 120 seconds.

The hardened microspheres can be concentrated by running a centrifugation cycle at 1500 G forces for approximately 5 minutes. The concentrated microsphere can optionally be washed by combining the concentrated microsphere suspension with sterile purified water, then re-concentrating using the same centrifugation cycle. The washing stage can be repeated multiple times to reduce the concentration of surfactant, solvent, and other residual process chemicals.

The washed and concentrated microspheres suspension can be prepared for long term storage by lyophilization. The concentrated suspension can be filled into lyophilization trays or directly into vials. Optionally, approximately 0.1 to 1% vol./vol. lyoprotectant solution consisting of about 0.2 g/mL sodium chloride may be added to prevent aggregation during lyophilization and subsequent processing steps in which the dry microspheres are handled. A suitable lyophilization cycle is applied to yield dry microspheres with less than 5% residual moisture.

The dry microspheres can be disaggregated using a jet milling process. The dry microspheres are fed into the mill at a controlled feed rate. Inside the mill, the dry microspheres are contacted a high pressure dry air stream at high velocity accelerating the aggregated particles. The collisions between the aggregated particles result in disaggregation of the microspheres. The jet mill injection pressure and dry microsphere feed rate can be selected so that the dry microspheres are disaggregated, but not damaged or otherwise altered by the milling process. The dry air and microspheres exit the jet mill where a cyclone can be used to recover the dry disaggregated microspheres from the exhaust stream.

The dry, disaggregated microspheres can be packaged in a vial of a suitable size and sealed with a low vapor transmission stopper and crimped aluminum cap. The sealed vial can be further packaged in a low vapor transmission, flexible foil pouch containing a desiccant. The packaged microspheres have suitable protection from moisture and oxygen yielding a shelf life of at least 1 year.

Procedure [B1]: Microspheres Having a Hydrophobic Surface—Oil Based Vehicle

Microspheres can be prepared by an oil-in-water emulsion technique. An organic phase can be prepared by dissolving dexamethasone acetate and 75/25 poly-lactic-co-glycolic acid in dichloromethane or ethyl acetate. An aqueous phase can be prepared by dissolving polyvinyl alcohol in deionized water. The deionized water can then be saturated with dichloromethane and dexamethasone acetate. The organic phase can be added to the aqueous phase with agitation with a high shear rotary immersion mixer to form an emulsion. The resulting oil-in-water emulsion can be further processed through a high shear microfluidizer to reduce the oil droplet size. The resulting emulsion can be added to an excess of deionized water and continuously agitated to harden the polymeric microspheres. After 60 minutes, the resulting microspheres can be isolated through 50 µm, 10 µm, and 1 µm filters. The particles collected on the 1 micron filter can be washed with deionized water, lyophilized, and then stored in sealed containers under refrigeration for further analysis. Sealed vials can be gamma irradiated prior to analysis or administration.

Injectable suspensions can be prepared in water (sterile water for injection) and in silicone oil. Particles are expected to settle in less than 1 hour in water but to remain as a stable suspension in silicone oil. The silicone oil is not expected to dissolve the polymeric microspheres.

In Vivo Studies

Epidural Administration in Canine Subjects Using Fluoroscopically-Guided Injection This approach is a modified version of that described by Cohen (vide supra). Male and female beagles can be acclimated and subjected to baseline neurologic and clinical chemistry examinations. Prior to treatment dogs can be anesthetized with propofol. The injection site can be shaved, and a 19-gauge epidural Touhy needle can be inserted at the L6-7 or L7-S1 interspace. A 22-gauge catheter can be threaded 8-10 cm to approximately the L2-L3 level. The position of the catheter can be verified by injection of contrast media under fluoroscopy. Two (2) mL of an aqueous suspension of microspheres, prepared according to the various procedures described herein, can be injected over a period of about 2 minutes. After about 10 minutes the catheter can be removed. Before and after surgery, subject baseline measurements can be obtained, including, for example, temperature and specific behavioral measures (pain tolerance, reflex, mobility, etc.). Before injection, and every 2 days after injection for 84 days, heart rate, blood pressure in the tail, spinal reflexes, sensory and pain responses, proprioception, gait and movement, cranial nerve function, and fundoscopic examination data can be recorded to observe the safety of the injected pharmaceutical composition. Blood samples can be collected prior to injection, then at 1, 2, 4, 8, 24, and 72 hour intervals after injection, and every 7 days thereafter to analyze for the pharmaceutical agent and its metabolized forms. At scheduled intervals, necropsy and histopathology can be performed as described by Cohen, vide supra, in a sub-set of animals.

Without wishing to be bound by theory, pharmaceutical compositions of the type described herein are not expected to elicit any significant or appreciable degree of inflammatory response or cause necrosis. Histological examination may reveal the microspheres to be localized and agglomerated within the epidural space at the site of injection with no evidence of the presence of the injection vehicle after about 2 days. Contents of the treated epidural pocket can be recovered by dissection. It can be reasonably expected that dexamethasone acetate will be released continuously over approximately 45 days under in vitro conditions of 1% C-TAB buffer at pH 3.5, with <20% of the drug released in 1 day, 30-60% in 7 days, 60-85% in 28 days and not less than 85% in 45 days, with complete microsphere polymer degradation in about 16 weeks/112 days.

Epidural Administration in Rabbits Using Fluoroscopically-Guided Injection

Pharmaceutical compositions of the type described herein can be used to reduce the risk of medical complications stemming from infarct. Rabbits can be prepared for treatment as described herein. A targeted injection location for the microspheres can be verified with contrast media prior to administration. Three rabbits can be given a 0.05-0.2 mL injection of a pharmaceutical composition prepared by Procedure [A3] herein that has an average particle size >10 um, directly into the common carotid artery (CCA) or internal carotid artery (ICA) that directly feeds the brain. Alternatively, rabbits can be given a corticosteroid drug product that is crystalline and not spherical, such as Depo-Medrol or Kenalog. For example, a pharmaceutical composition with a particle size <10 um as prepared by Procedure [A1], can be used for comparison. Before injection and every 6 hours after each injection, heart rate, neurological deficit scoring, spinal reflexes, and body temperature can be measured. After 72 hours, necropsy/histopathology can be performed as described herein to determine the degree of infarct, if any, present in subjects injected with the larger microsphere composition.

It can be reasonably expected that animals injected with microspheres having an average size of less than 10 µm will not show a difference in behavior or vitality over the 72 hour period, nor will their vital signs change drastically. In contrast, animals injected with the larger microsphere compositions or crystalline drugs may exhibit signs of paralysis or death.

Intravitreal Injections in Rabbit

Anesthetized New Zealand Dutch Belted rabbits can be used in this study; topical antibiotic drops can be applied to the treated eyes, and 0.1 mL of the microsphere composition prepared in Procedure [B1] can be injected via a 25 gauge needle into the vitreous body in either an aqueous vehicle, [C-a] or silicone oil [C-s]. Prior to treatment, baseline fundus photos can be taken and an ophthalmic examination can be performed. At scheduled times, animals can be euthanized and the vitreous body of the treated eyes removed by dissection. The microspheres can be isolated from the vitreous fluid. Drug content of vitreous fluid and isolated microspheres can be assayed using techniques known in the art. In a second rabbit population, whole eyes can be enucleated and frozen. Cryomicrotome sections can be taken of the frozen eyes to determine location and size domain of injection contents.

The microspheres from the [C-a] injection are expected to be dispersed in various regions of the vitreous after 7 days. In contrast, the microspheres from the [C-s] formulation are expected to be found localized at the site of injection for over 60 days.

All publications, patents, and patent applications are incorporated herein by reference. While in the foregoing specification this invention has been described in relation to certain specific embodiments thereof, and many details have been set forth for purposes of illustration, it will be apparent to those skilled in the art that the present invention is susceptible to additional embodiments, and that certain of the details described herein may be varied considerably without departing from the basic principles of the present invention.

The present invention provides for the following embodiments, the numbering of which is not to be construed as designating levels of importance:

Embodiment 1 relates to a plurality of substantially spherical microspheres comprising: at least one API substantially dispersed in at least one polymer and a lyoprotectant on an outside surface of the plurality of substantially spherical microspheres, wherein the plurality of substantially spherical microspheres have: a D99[num] particle diameter of less than about 10 µm; a D99[num] circularity value of from about 0.8 to about 1.0; and comprise API in a weight of about 20 to about 40 wt. % of the polymer.

Embodiment 2 relates to the microspheres of Embodiment 1, wherein the microspheres have a D50[num] particle diameter of about 1 µm to about 4 µm.

Embodiment 3 relates to the microspheres of Embodiments 1-2, wherein the microspheres have a D100[num] particle diameter of less than about 15 µm.

Embodiment 4 relates to the microspheres of Embodiments 1-3, wherein the microspheres have a D90[num] circularity value of from about 0.95 to about 1.0.

Embodiment 5 relates to the microspheres of Embodiments 1-4, wherein the plurality of microspheres has low porosity.

Embodiment 6 relates to the microspheres of Embodiments 1-5, wherein the at least one API treats pain.

Embodiment 7 relates to the microspheres of Embodiment 6, wherein the at least one API is at least one of an opioid, an anti-inflammatory, a calcium channel blocker, a xanthine oxidase inhibitor, an antibiotic, or a hormone.

Embodiment 8 relates to the microspheres of Embodiment 7, wherein the anti-inflammatory is at least one of a non-steroidal anti-inflammatory drug (NSAID), a COX-2 specific inhibitor, a disease modifying anti-rheumatic drug (DMARD), or a corticosteroid or an ester thereof.

Embodiment 9 relates to the microspheres of Embodiment 7, wherein the anti-inflammatory is a synthetic, glucocorticoid steroid.

Embodiment 10 relates to the microspheres of Embodiment 9, wherein the synthetic, glucocorticoid steroid is dexamethasone acetate, 9 alpha-fluoro-11-beta, 17-alpha, 21-trihydroxy-16 alpha-methylpregna-1,4-diene-3,20-dione 21-acetate Embodiment 11 relates to the microspheres of Embodiments 1-10, wherein the at least one polymer comprises an amphiphilic block copolymer.

Embodiment 12 relates to the microspheres of Embodiments 1-11, wherein the at least one polymer is a copolymer of lactic acid and glycolic acid (PLGA).

Embodiment 13 relates to the microspheres of Embodiments 1-12, wherein the at least one polymer comprises at least one of PLGA-block-PEG and PLGA.

Embodiment 14 relates to the microspheres of Embodiments 1-13, wherein the microspheres are at least one of biodegradable, bioerodible, and biocompatible.

Embodiment 15 relates to an injectable composition comprising the plurality of microspheres of Embodiments 1-14 and a vehicle.

Embodiment 16 relates to the composition of Embodiment 15, wherein the at least one API is substantially dispersed in the polymer and the composition is otherwise substantially free of API that is insoluble in the vehicle.

Embodiment 17 relates to the injectable composition of Embodiments 15-16, wherein the plurality of microspheres release about 2% to about 30% of the API within 48 hours following administration of the injectable composition to a subject; and release the at least one API over a period of from about 14 to about 120 days.

Embodiment 18 relates to the injectable composition of Embodiments 15-17, wherein the vehicle is a liquid vehicle.

Embodiment 19 relates to the injectable composition of Embodiments 15-18, wherein the vehicle is an aqueous vehicle.

Embodiment 20 relates to the injectable composition of Embodiments 15-19, wherein the injectable composition further comprises at least one pharmaceutically acceptable excipient.

Embodiment 21 relates to the injectable composition of Embodiments 15-20, wherein the plurality of microspheres are present in a concentration of about 1 mg/mL to about 500 mg/mL in the vehicle.

Embodiment 22 relates to a method for treating headache, radiculopathy, back pain, ankylosing spondylosis, inflammation, epilepsy, neuropathic pain, hot flashes, restless leg syndrome, multiple sclerosis, vasospasm, myofascial gravis, joint pain, gout, rheumatoid arthritis, trigeminal neuralgia or pelvis organ prolapse comprising administering the injectable composition of Embodiments 15-21.

Embodiment 23 relates to the method of Embodiment 22, wherein the administration is carried out no more than once per about 14 days.

Embodiment 24 relates to the method of Embodiment 23, wherein the administration is carried out no more than once per about 56 days.

Embodiment 25 relates to an injectable composition of Embodiments 15-21 for use in a method for treating headache, radiculopathy, back pain, ankylosing spondylosis, inflammation, epilepsy, neuropathic pain, hot flashes, restless leg syndrome, multiple sclerosis, vasospasm, myofascial gravis, joint pain, gout, rheumatoid arthritis, trigeminal neuralgia or pelvis organ prolapse.

Embodiment 26 relates to the injectable composition of Embodiment 25, wherein the composition is administered no more than once per about 14 days.

Embodiment 27 relates to the injectable composition of Embodiment 25, wherein the composition is administered no more than once per about 56 days.

What is claimed is:

1. A plurality of substantially spherical microspheres comprising:
   at least one API substantially dispersed in at least one polymer, wherein the at least one polymer comprises at least one polyhydroxyalkanoate polymer and a lyoprotectant, which is a salt, on an outside surface of the plurality of substantially spherical microspheres, wherein the plurality of substantially spherical microspheres have:
   a D99[num] particle diameter of less than about 10 µm;
   a D90[num] circularity value of from about 0.8 to about 1.0; and
   comprise API in a weight of about 20 to about 40 wt. % of the polymer.

2. The microspheres of claim 1, wherein the at least one polyhydroxyalkanoate polymer comprises a block copolymer.

3. The microspheres of claim 1, wherein the microspheres have a D50[num] particle diameter of about 1 µm to about 4 µm.

4. The microspheres of claim 1, wherein the microspheres have a D100[num] particle diameter of less than about 15 μm.

5. The microspheres of claim 1, wherein the microspheres have a D90[num] circularity value of from about 0.95 to about 1.0.

6. The microspheres of claim 1, wherein the at least one API treats pain.

7. The microspheres of claim 6, wherein the at least one API is at least one of an opioid, an anti-inflammatory, a calcium channel blocker, a xanthine oxidase inhibitor, an antibiotic, or a hormone.

8. The microspheres of claim 7, wherein the anti-inflammatory is a synthetic, glucocorticoid steroid.

9. The microspheres of claim 8, wherein the synthetic, glucocorticoid steroid is dexamethasone acetate, 9 alpha-fluoro-11-beta, 17-alpha, 21-trihydroxy-16 alpha-methyl-pregna-1,4-di ene-3,20-dione 21-acetate 10. The microspheres of claim 1, wherein the microspheres are at least one of biodegradable, bioerodible, and biocompatible.

11. An injectable composition comprising the plurality of microspheres of claim 1 and a vehicle.

12. The composition of claim 11, wherein the at least one API is substantially dispersed in the polymer and the composition is otherwise substantially free of API that is insoluble in the vehicle.

13. The injectable composition of claim 11, wherein the plurality of microspheres release about 2% to about 30% of the API within 48 hours following administration of the injectable composition to a subject; and
release the at least one API over a period of from about 14 to about 120 days.

14. The injectable composition of claim 11, wherein the vehicle is a liquid vehicle.

15. The injectable composition of claim 11, wherein the vehicle is an aqueous vehicle.

16. The injectable composition of claim 11, wherein the injectable composition further comprises at least one pharmaceutically acceptable excipient.

17. The injectable composition of claim 11, wherein the plurality of microspheres are present in a concentration of about 1 mg/mL to about 500 mg/mL in the vehicle.

18. The injectable composition of claim 11 for use in a method for treating headache, radiculopathy, back pain, ankylosing spondylosis, inflammation, epilepsy, neuropathic pain, hot flashes, restless leg syndrome, multiple sclerosis, vasospasm, myofascial gravis, joint pain, gout, rheumatoid arthritis, trigeminal neuralgia or pelvis organ prolapse.

19. The injectable composition of claim 18, wherein the composition is administered in a bolus.

20. The injectable composition of claim 19, wherein the composition is administered no more than once per about 14 days.

21. The microspheres of claim 1, wherein the polyhydroxyalkanoate polymer comprises poly(hydroxybutyrate).

* * * * *